US012669489B2

(12) United States Patent
Yu

(10) Patent No.: US 12,669,489 B2
(45) Date of Patent: Jun. 30, 2026

(54) WATER QUALITY DETECTION SYSTEM AND DETECTION METHOD THEREOF

(71) Applicant: Industrial Technology Research Institute, Hsinchu (TW)

(72) Inventor: Yi-Hsin Yu, Hsinchu City (TW)

(73) Assignee: Industrial Technology Research Institute, Hsinchu (TW)

( * ) Notice: Subject to any disclaimer, the term of this patent is extended or adjusted under 35 U.S.C. 154(b) by 493 days.

(21) Appl. No.: 18/302,768

(22) Filed: Apr. 18, 2023

(65) Prior Publication Data

US 2024/0210372 A1     Jun. 27, 2024

(30) Foreign Application Priority Data

Dec. 23, 2022     (TW) ................................. 111149757

(51) Int. Cl.
*G01N 33/18*         (2006.01)
*G01N 35/00*         (2006.01)
*G01N 35/04*         (2006.01)

(52) U.S. Cl.
CPC ... *G01N 33/18* (2013.01); *G01N 2035/00108* (2013.01); *G01N 2035/0432* (2013.01); *G01N 2035/0484* (2013.01)

(58) Field of Classification Search
CPC . G01N 2035/00108; G01N 2035/0432; G01N 2035/0484; G01N 33/18; G01N 2021/478; G01N 2021/7759; G01N 33/48764; G01N 33/50; G01N 33/54387; G01N 2201/0256; G01N 2203/0447; G01N 2021/0353; G01N 2021/845; G01N 23/2204; G01N 35/04; G01N 2035/0422;

G01N 2223/643; G01N 2223/642; G01N 33/52; G01N 21/251; G01N 21/255; Y10S 435/805; B01L 2300/0825
USPC .......................... 73/53.01, 61.43, 863.92, 41
See application file for complete search history.

(56) References Cited

U.S. PATENT DOCUMENTS

| | | | |
|---|---|---|---|
| 11,079,368 B2 | 8/2021 | Spada et al. | |
| 2016/0216285 A1* | 7/2016 | Takai | G01N 35/00029 |
| 2016/0232421 A1* | 8/2016 | Decker | G01N 21/78 |
| 2022/0299445 A1* | 9/2022 | Ko | G01N 21/8483 |

FOREIGN PATENT DOCUMENTS

| | | |
|---|---|---|
| CN | 103335955 | 10/2013 |
| CN | 108760728 | 11/2018 |
| EP | 0646784 | 4/1995 |

(Continued)

*Primary Examiner* — John E Breene
*Assistant Examiner* — Truong D Phan
(74) *Attorney, Agent, or Firm* — JCIPRNET

(57)     ABSTRACT

A water quality detection system includes a conveying module, multiple detection test papers, a supply module, a detection module, and a processing unit. The detection test papers are disposed on the conveying module in a continuous arrangement. The conveying module conveys the detection test papers along a conveying path to sequentially pass through a first position and a second position. The supply module supplies liquid to be tested to the detection test papers passing through the first position. The detection module captures a color signal of the detection test papers passing through the second position. The processing unit generates a water quality signal according to the color signal.

12 Claims, 3 Drawing Sheets

(56)         References Cited

FOREIGN PATENT DOCUMENTS

| | | | |
|---|---|---|---|
| TW | 201428293 A | * | 7/2014 |
| TW | I595079 | | 8/2017 |
| TW | 201925778 | | 7/2019 |
| TW | M592966 | | 4/2020 |
| TW | 202032107 | | 9/2020 |
| TW | I718498 | | 2/2021 |
| TW | M617481 | | 9/2021 |
| TW | M626507 | | 5/2022 |
| TW | M641800 | | 6/2023 |

* cited by examiner

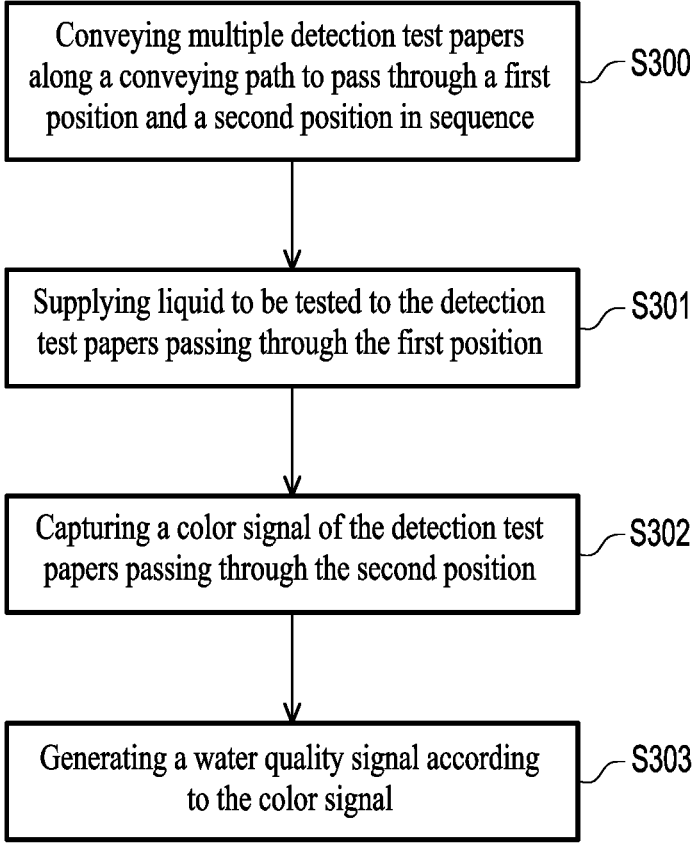

Conveying multiple detection test papers along a conveying path to pass through a first position and a second position in sequence — S300

Supplying liquid to be tested to the detection test papers passing through the first position — S301

Capturing a color signal of the detection test papers passing through the second position — S302

Generating a water quality signal according to the color signal — S303

FIG. 3

WATER QUALITY DETECTION SYSTEM AND DETECTION METHOD THEREOF

CROSS-REFERENCE TO RELATED APPLICATION

This application claims the priority benefit of Taiwan application serial no. 111149757, filed on Dec. 23, 2022. The entirety of the above-mentioned patent application is hereby incorporated by reference herein and made a part of this specification.

TECHNICAL FIELD

The disclosure relates to a detection system and a detection method, and in particular to a water quality detection system and a detection method thereof.

BACKGROUND

Generally, a pH detection device is a contact device, so the pH value can only be determined by in contact with sewage. In addition, the pH sensor in the contact device needs to be calibrated, cleaned, and replaced regularly after use. Therefore, the maintenance cost is high, and if lack of maintenance, many problems will occur that cause the measurement value to be unstable. If the sampled sewage is strong acid or strong alkali, once the maintenance work of the pH sensor is not complete, the pH sensor is easily affected by the residual liquid.

SUMMARY

The disclosure provides a water quality detection system, which includes a conveying module, multiple detection test papers, a supply module, a detection module, and a processing unit. The detection test papers are disposed on the conveying module in a continuous arrangement. The conveying module conveys the detection test papers along a conveying path to sequentially pass through a first position and a second position. The supply module supplies liquid to be tested to the detection test papers passing through the first position. The detection module captures a color signal of the detection test papers passing through the second position. The processing unit generates a water quality signal according to the color signal.

The disclosure further provides a detection method of a water quality detection system, which includes: multiple detection test papers are conveyed along a conveying path to sequentially pass through a first position and a second position; liquid to be tested is supplied to the detection test papers passing through the first position; a color signal of the detection test papers passing through the second position are captured; and a water quality signal is generated according to the color signal.

In order to make the aforementioned features and advantages of the disclosure comprehensible, embodiments accompanied with drawings are described in detail as follows.

BRIEF DESCRIPTION OF THE DRAWINGS

FIG. 3 is a flowchart of steps of a detection method of a water quality detection system according to an embodiment of the disclosure.

DETAILED DESCRIPTION OF DISCLOSURED EMBODIMENTS

Figure 1:
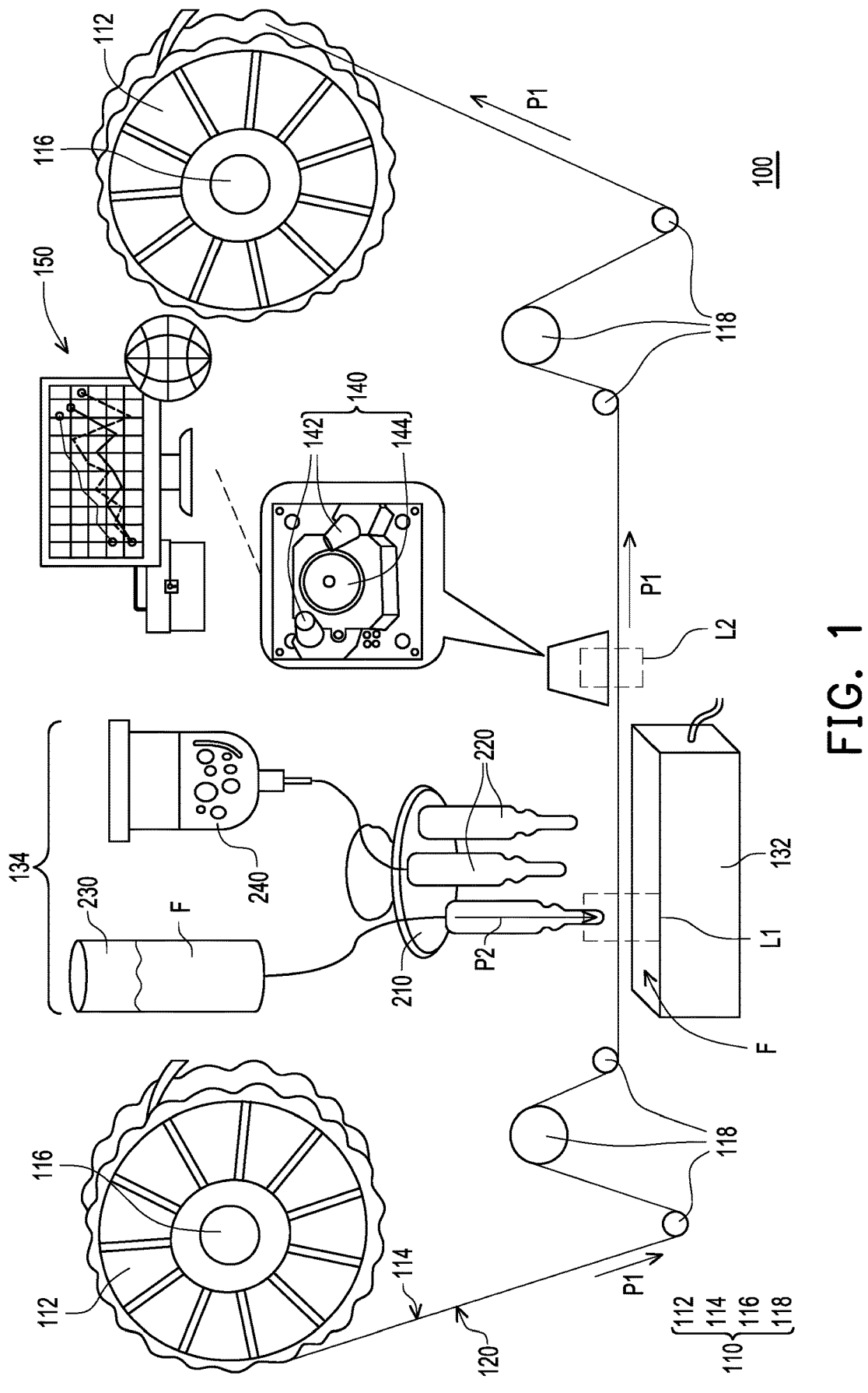
FIG. 1 is a schematic diagram of a water quality detection system according to an embodiment of the disclosure.

FIG. 1 is a schematic diagram of a water quality detection system according to an embodiment of the disclosure. Please refer to FIG. 1. The embodiment provides a water quality detection system 100, which includes a conveying module 110, detection test papers 120, a supply module 130, a detection module 140, and a processing unit 150. The water quality detection system 100 is configured to detect liquid F to be tested and obtain a water quality signal thereof. The liquid F to be tested is, for example, tap water, rainwater, river water, sewage or other water sources, and the water quality signal is, for example, an acid-base value (pH value) of the liquid F to be tested.

For example, the conveying module 110 includes two rollers 112, a conveyor belt 114, and a driving element 116. The conveyor belt 114 is connected between the two rollers 112, and the driving element 116 is connected to at least one of the two rollers 112 and configured to drive the two rollers 112 to drive the conveyor belt 114 to pass along a conveying path P1 and sequentially pass through a first position L1 and a second position L2. In the embodiment, the conveying module 110 further includes at least one positioning post 118, configured to allow the conveyor belt 114 to abut against the positioning post 118 to pass along the conveying path P1. The conveying path P1 may be designed in different shapes and sizes according to the structural configuration of each part of the conveying module 110. The disclosure does not limit the actual route shape for conveyance of the conveying path P1 and the overall size of the conveying module 110.

The detection test papers 120 are disposed on the conveying module 110 in a continuous arrangement, and the conveying module 110 conveys the detection test papers 120 along the conveying path P1 to sequentially pass through the first position L1 and the second position L2. The detection test paper 120 is, for example, a universal test paper, configured to produce a color change through a chemical reaction after in contact with the liquid F to be tested, and then correspond to different color signals for the use of analysis. In detail, in the embodiment, the detection test papers 120 are disposed in a paper roll shape on the conveyor belt 114 on the roller 112, and are unfolded along the conveyor belt 114 along the conveying path P1 by the rotation of the roller 112.

The supply module 130 supplies the liquid F to be tested to the detection test paper 120 passing through the first position L1. For example, in the embodiment, the supply module 130 includes a carrier box 132 and a supply device 134. The carrier box 132 carries the liquid F to be tested, so that the detection test paper 120 passes along the conveying path P1. The supply device 134 supplies the liquid F to be tested to the carrier box 132. In the embodiment, the supply device 134 and the carrier box 132 are located on opposite sides of the conveyor belt 114, the supply device 134 supplies the liquid F to be tested along a supply path P2, and the carrier box 132 is located on the supply path P2. Therefore, the liquid F to be tested may be supplied to the first position L1 in a non-contact manner and then fall into the carrier box 132. In the embodiment, the carrier box 132 has a draining function, and the disclosure does not limit the component or method for draining. That is, the carrier box 132 has the function of allowing the liquid F to be tested to flow continuously.

In detail, in the embodiment, the supply device 134 includes a turntable 210, multiple droppers 220, a sample device 230, and a cleaning device 240. The droppers 220 are disposed on the turntable 210, and the sample device 230 supplies the liquid F to be tested to the droppers 220. The cleaning device 240 supplies cleaning liquid to the droppers 220. Therefore, driven by the turntable 210, the dropper 220 containing the liquid F to be tested reaches the supply path P2 to supply the liquid F to be tested to the detection test paper 120 passing through the first position L1. After the supply is completed, driven by the turntable 210, the dropper 220 is switched away from the supply path P2 to the path for supplying the cleaning liquid, and the dropper 220 after use is cleaned by the cleaning liquid supplied by the cleaning device 240, so as to facilitate subsequent repeated use, thereby realizing the effect of continuously supplying the liquid F to be tested to the detection test paper 120 passing through the first position L1. In different embodiments, the supply device 134 may also be used in combination with sampling devices such as pumping motors and sponge filters, and the disclosure is not limited thereto.

The detection module 140 captures a color signal of the detection test papers 120 passing through the second position L2. In detail, in the embodiment, the detection module 140 includes an illuminating device 142 and an image capturing device 144. The illuminating device 142 provides an illuminating light beam to the detection test papers 120 passing through the second position L2 and is configured to provide a light source to improve the sensing effect of the image capturing device 144. The image capturing device 144 is configured to capture the color state of the detection test paper 120 after in contact with the liquid F to be tested and undergoing a chemical change. The illuminating device 142 is, for example, a white light-emitting diode (White LED), an ultraviolet light-emitting diode (UV LED), or a near infrared light-emitting diode (NIR LED), a laser diode, a halogen lamp or a tungsten lamp, and the disclosure is not limited thereto. The image capturing device 144 captures the detection test papers 120 passing through the second position L2 to obtain a color signal. The image capturing device 144 is, for example, a color reader, an optical wavelength spectrometer or a spectroscope, and the disclosure is not limited thereto.

The processing unit 150 generates a water quality signal according to the color signal obtained by the image capturing device 144. The processing unit 150 is, for example, a central processing unit (CPU), or other programmable general-purpose or special-purpose microprocessors, digital signal processors (DSPs), programmable controllers, application specific integrated circuits (ASICs), or other similar elements or a combination thereof, and the disclosure is not limited thereto. The detection module 140 may transmit the color signal to the processing unit 150 directly, indirectly, or wirelessly through electrical connection, and the disclosure is not limited thereto.

Therefore, by means of the configuration described above, that is, the conveying module 110 conveys the detection test papers 120 along the conveying path P1 to pass through the first position L1 and be in contact with the liquid F to be tested, and to pass through the second position L2 for color signal capturing, thereby obtaining the water quality signal of the liquid F to be tested. In this way, the water quality detection system 100 that is non-contact may be provided to reduce maintenance frequency. Moreover, the water quality detection system 100 may realize continuous detection, continuous identification of detection results, and simultaneous detection and identification, so as to improve detection efficiency and quality. In an embodiment, the water quality detection system 100 may further include a protective shell (not shown), which has an accommodating space, and at least one of the conveying module 110, the supply module 130, the detection module 140, and the processing unit 150 is disposed in the accommodating space to achieve the effect of protection, reduction in ambient light, and improvement in detection quality. The disclosure does not limit the material, size, type, and contained components of the protective shell.

Figure 2:
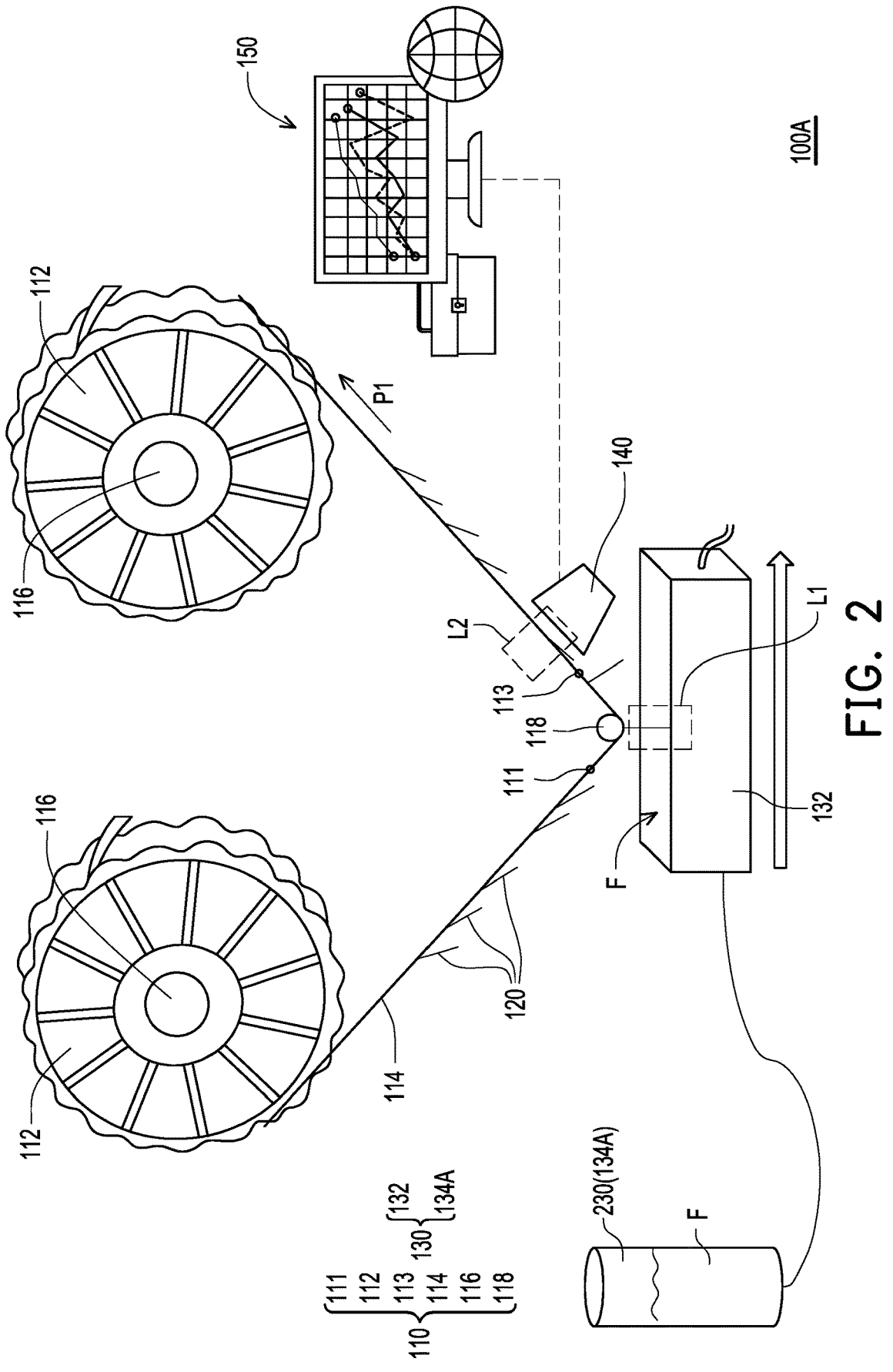
FIG. 2 is a schematic diagram of a water quality detection system according to another embodiment of the disclosure.

FIG. 2 is a schematic diagram of a water quality detection system according to another embodiment of the disclosure. Please refer to FIG. 2. A water quality detection system 100A of the embodiment is similar to the water quality detection system 100 shown in FIG. 1. The difference between the two is that in the embodiment, a supply device 134A is connected to the carrier box 132 and directly supplies the liquid F to be tested to the carrier box 132. Specifically, in the embodiment, the supply device 134A merely includes the sample device 230. In this way, the volume and number of components of the supply device 134A may be saved.

In addition, in the embodiment, the conveying module 110 further includes a differentiation element 111 and a binding element 113. Both the differentiation element 111 and the binding element 113 are disposed on the conveying path P1. The differentiation element 111 is configured to separate one end of the detection test papers 120 from the conveyor belt 114 and passes through the first position L1, and the binding element 113 is configured to tighten the detection test papers 120 to be attached to the conveyor belt 114 in parallel and passes through the second location L2. The differentiation element 111 and the binding element 113 are, for example, ring-shaped structures, but the disclosure is not limited thereto.

In detail, in the embodiment, the detection test papers 120 are attached to the conveyor belt 114 in parallel during the initial conveyance, and are conveyed to the first position L1 (or just before entering the first position L1) along the conveying path P1 by the conveying module 110. At this time, by means of the differentiation element 111, one end of the detection test paper 120 that is originally parallel to the conveyor belt 114 may be lifted in sequence, so that the lifted end of the detection test paper 120 is stretched in a suspended state away from the conveyor belt 114 to increase the contactable area and ensure complete contact with the liquid F to be tested. The detection test papers 120 from the first position L1 are conveyed to the second position L2 (or just before entering the second position L2) along the conveying path P1 by the conveying module 110. At this time, by means of the binding element 113, the detection test paper 120 that is originally in a suspended state may be bundled in sequence, so that the detection test paper 120 may be restored to the state of being attached to the conveyor belt 114 in parallel, so as to increase the area parallel to the plane of the conveyor belt 114, thereby increasing the captureable area of the detection module 140 and improving detection quality. In this way, the water quality detection system 100A that is non-contact may be provided to reduce maintenance frequency. Moreover, the water quality detection system 100A may realize continuous detection, continuous identification of detection results, and simultaneous detection and identification, so as to improve detection efficiency and quality.

FIG. 3 is a flowchart of steps of a detection method of a water quality detection system according to an embodiment of the disclosure. Please refer to FIG. 3. The detection method of the embodiment may be applied to at least the water quality detection system 100 shown in FIG. 1 or the water quality detection system 100A shown in FIG. 2. For the convenience of description, the following paragraphs take the description of the water quality detection system 100 shown in FIG. 1 as an example. The embodiment provides a detection method of the water quality detection system 100. First, step S300 is performed, in which the detection test papers 120 are conveyed along the conveying path P1 to pass through the first position L1 and the second position L2 in sequence. Next, after the above step, step S301 is performed, in which the liquid F to be tested is supplied to the detection test papers 120 passing through the first position L1. Next, after the above step, step S302 is performed, in which the color signal of the detection test papers 120 passing through the second position L2 are captured. Finally, after the above step, the water quality signal is generated according to the color signal.

Therefore, through the detection method implemented above, that is, the detection test papers 120 are conveyed along the conveying path P1 to pass through the first position L1 and be in contact with the liquid F to be tested, and to pass through the second position L2 for color signal capturing, thereby obtaining the water quality signal of the liquid F to be tested. In this way, maintenance frequency may be reduced, continuous detection and continuous identification of detection results may be realized, and detection and identification may be performed simultaneously to improve detection efficiency and quality.

To sum up, in the water quality detection system and the detection method of the disclosure, the water quality detection system includes a conveying module, detection test papers, a supply module, a detection module, and a processing unit. The conveying module conveys multiple detection test papers along the conveying path to pass through the first position and be in contact with the liquid to be tested, and to pass through the second position for color signal capturing, thereby obtaining the water quality signal of the liquid to be tested. In this way, a non-contact water quality detection system may be realized to reduce maintenance frequency. Moreover, the water quality detection system may realize continuous detection, continuous identification of detection results, and simultaneous detection and identification, so as to improve detection efficiency and quality.

Although the disclosure has been described with reference to the above embodiments, the described embodiments are not intended to limit the disclosure. People of ordinary skill in the art may make some changes and modifications without departing from the spirit and the scope of the disclosure. Thus, the scope of the disclosure shall be subject to those defined by the attached claims.

What is claimed is:
1. A water quality detection system, comprising:
a conveying module, comprising:
   two rollers;
   a conveyor belt, connected between the two rollers;
   a driving element, connected to at least one of the two rollers, and configured to drive the two rollers to drive the conveyor belt to pass along a conveying path and pass through a first position and a second position in sequence; and
   a differentiation element, disposed on the conveying path, configured to separate one end of the plurality of detection test papers from the conveyor belt, and passing through the first position;
a plurality of detection test papers, disposed on the conveying module in a continuous arrangement, and the conveying module conveying the plurality of detection test papers along the conveying path to sequentially pass through the first position and the second position;
a supply module, supplying liquid to be tested to the plurality of detection test papers passing through the first position;
a detection module, capturing a color signal of the plurality of detection test papers passing through the second position; and
a processing unit, generating a water quality signal according to the color signal.
2. The water quality detection system according to claim 1, wherein the conveying module further comprises:
   at least one positioning post, the conveyor belt abutting against the at least one positioning post to pass along the conveying path.
3. The water quality detection system according to claim 1, wherein the supply module comprises:
   a carrier box, carrying the liquid to be tested; and
   a supply device, supplying the liquid to be tested to the carrier box.
4. The water quality detection system according to claim 3, wherein the supply device and the carrier box are located on opposite sides of the conveyor belt, the supply device supplies the liquid to be tested along a supply path, and the carrier box is located on the supply path.
5. The water quality detection system according to claim 4, wherein the supply device comprises:
   a turntable;
   a plurality of droppers, disposed on the turntable and switched to the supply path driven by the turntable;
   a sample device, supplying liquid to be tested to the plurality of droppers; and
   a cleaning device, supplying cleaning liquid to the plurality of droppers.
6. The water quality detection system according to claim 3, wherein the supply device is connected to the carrier box, and directly conveys the liquid to be tested to the carrier box.
7. The water quality detection system according to claim 1, wherein the detection module comprises:
   an illuminating device, providing an illuminating light beam to the plurality of detection test papers passing through the second position; and
   an image capturing device, capturing the plurality of detection test papers passing through the second position to obtain the color signal.
8. The water quality detection system according to claim 1, wherein the water quality signal comprises an acid-base value (pH value) of liquid to be tested.
9. The water quality detection system according to claim 1, wherein the conveying module further comprises:
   a binding element, disposed on the conveying path, configured to tighten the plurality of detection test papers so as to be attached to the conveyor belt in parallel, and passing through the second position.
10. The water quality detection system according to claim 1, further comprising:
   a protective shell, having an accommodating space, and at least one of the conveying module, the supply module, the detection module, and the processing unit being disposed in the accommodating space.

11. A detection method of a water quality detection system, wherein the water quality detection system comprise a conveying module, the conveying module comprise two rollers, a conveyor belt and a driving element, the conveyor belt is connected between the two rollers, the driving element is connected to at least one of the two rollers, and configured to drive the two rollers to drive the conveyor belt, the detection method comprising:

conveying a plurality of detection test papers along a conveying path to sequentially pass through a first position and a second position;

separating one end of the plurality of detection test papers from a conveyor belt;

supplying liquid to be tested to the plurality of detection test papers passing through the first position;

bundle the plurality of detection test papers to be attached to the conveyor belt in parallel;

capturing a color signal of the plurality of detection test papers passing through the second position; and generating a water quality signal according to the color signal.

12. The detection method of the water quality detection system according to claim 11, wherein a method of supplying the liquid to be tested to the plurality of detection test papers passing through the first position further comprises:

supplying the liquid to be tested to a plurality of droppers;

switching the plurality of droppers to a supply path to supply the liquid to be tested;

switching the plurality of droppers away from the supply path; and supplying cleaning liquid to the plurality of droppers.

* * * * *